United States Patent [19]

Lewis et al.

[11] Patent Number: 4,647,772
[45] Date of Patent: Mar. 3, 1987

[54] MASS SPECTROMETERS

[75] Inventors: Ivor A. S. Lewis, Knutsford; David C. Smith, Northwich, both of United Kingdom

[73] Assignee: VG Instruments Group Limited, Crawley, United Kingdom

[21] Appl. No.: 704,283

[22] Filed: Feb. 22, 1985

[30] Foreign Application Priority Data

Feb. 22, 1984 [GB] United Kingdom ............... 8404683

[51] Int. Cl.[4] ........................................ D01D 59/44
[52] U.S. Cl. .................................. 250/288; 250/281; 250/282
[58] Field of Search ............ 250/281, 282, 288, 423 R

[56] References Cited

U.S. PATENT DOCUMENTS

| 4,209,696 | 6/1980 | Fite | 250/288 |
|---|---|---|---|
| 4,239,967 | 12/1980 | Carr et al. | 250/288 |
| 4,281,246 | 7/1981 | White et al. | 250/288 |
| 4,298,795 | 11/1981 | Takeachi et al. | 250/288 |
| 4,300,044 | 11/1981 | Iribarme et al. | 250/288 |
| 4,542,293 | 9/1985 | Fenn et al. | 250/288 |

FOREIGN PATENT DOCUMENTS

WO81/03394 11/1981 PCT Int'l Appl.

OTHER PUBLICATIONS

McFadden, W. H., "Interfacing Chromatography and Mass Spectrometry", Journal of Chromatographic Science, vol. 17, Jan. 1979, pp. 2-16.
Arpino, P. J. & Guiochon, G., "LC/MS Coupling", Analytical Chemistry, vol. 51, No. 7, Jun. 1979, pp. 682A-700A.
Yorke, D. A., "Liquid Chromatography-Mass Spectrometry", Proc. Inst. Petrol (London), vol. 2, 1982, pp. 159-170.
Blakley, C. R. et al., "A New Soft Ionization Technique for Mass Spectrometry of Complex Molecules", American Chemical Society, vol. 102, 1980, pp. 5931-5933.
Blakley, C. R. et al., "A New Soft Ionization Technique for Mass Spectrometry of Complex Molecules, 28th Annual Conference on Mass Spectrometry and Allied Topics, 1980, pp. 320-321.
Blakley et al., "Thermospray Interface for Liquid Chromatography/Mass Spectrometry", Analytical Chemistry, vol. 55, 1983, pp. 750-754.
Vestal, M. L., "Studies of Ionization Mechanisms Involved in Thermospray LC-MS", International Journal of Mass Spectrometry and Ion Physics, vol. 46, 1983, pp. 193-196.
Vestal, M. L., "Recent Advances in Thermospray LC-MS", 31st Annual Conference on Mass Spectrometry and Allied Topics, 1983, pp. 108-110.
Yergey, A. L. et al., "Direct Analysis of Intractable Endogeneous Molecules by Thermospray LC/MS 31st Annual Conference on Mass Spectrometry and Allied Topics, 1983, pp. 860-861.

List Continued on next page.

Primary Examiner—Bruce C. Anderson
Attorney, Agent, or Firm—Schwartz, Jeffery, Schwaab, Mack, Blumenthal & Evans

[57] ABSTRACT

A mass spectrometer having a thermospray ion source, suitable for the analysis of liquid samples is disclosed. The source comprises a strongly heated atomizing nozzle (4) through which the sample is pumped into a spray chamber (5, 11), and an aperture in a cone (26), through which the ions pass through an electrostatic lens (15, 16, 17) into a region (23) in which a mass analyzer is situated. Electrode means (27, 45) generate a repulsive electrostatic field which improves the efficiency of the transmission of ions through the hole in the cone (26). The electrode is situated downstream of the hole in cone (26). By further increasing the potential on the electrode (27, 45) the nature of the ions passing through the hole in the cone (26) can be changed from largely adduct and cluster ions formed by association of solvent molecules with sample ions in the thermospray to largely pseudomolecular sample ions similar to those formed by conventional chemical ionization.

7 Claims, 7 Drawing Figures

OTHER PUBLICATIONS

Liberato, D. J. et al., "Characterization of Glucuronides with a Thermospray Liquid Chromatography/Mass Spectrometry Interface, Analytical Chemistry, vol. 55, 1983, pp. 1741–1744.

McFadden, W. H., "Thermospray LC/MS: Supplement or Substitute for Existing Techniques", Finnigan Spectra, vol. 9, No. 1, 1983, pp. 23–28.

covey, T. et al., "Direct Liquid Introduction/Thermospray Interface for Liquid Chromatography/Mass Spectrometry", Anal. Chem., vol. 55, 1983, pp. 2275–2280.

Henion, J., "Thermospray LC/MS Progress with a Commercially Available GC/MS", 31st Annual Conference on Mass Spectrometry and Allied Topics, 1983, pp. 862–863.

MASS SPECTROMETERS

BACKGROUND TO THE INVENTION

1. Field of the Invention

This invention relates to a mass spectrometer incorporating an ion source adapted for the analysis of solutions, especially the eluent from a liquid chromatographic column, and to such a source. More particularly it relates to a thermospray type of liquid chromatograph-mass spectrometer interface in which the solvent is removed and the sample is ionized through the generation by thermal means of a spray containing electrically charged species.

2. Related Art

The use of a mass spectrometer to analyse the eluent from liquid chromatographic columns presents many difficulties, and a wide variety of methods have been proposed in the last few years. These have been reviewed by W. H. McFadden in Journal of Chromatographic Science, 1979, vol. 17, pps. 2-16, by P. J. Arpino and G. Guiochon in Analytical Chemistry, 1979, volume 51, pps. 638A-701A, and by D. A. Yorke in Proc. Inst. Petrol. (London), 1982, vol. 2, pps 159-170. A major problem encountered when combining a liquid chromatograph with a mass spectrometer is that the eluent from a typical liquid chromatograph may consist of several ml/minute of a very dilute solution, frequently in an aqueous solvent, while most mass spectrometer ion sources operate in a high vacuum and can accept only a very small quantity of such a solution, typically not exceeding 0.1 ml/minute. In order to avoid excessive loss of sample, therefore, the interface between the chromatograph and the ion source must be capable of removing a large proportion of the solvent while transmitting the bulk of the sample. Further, liquid chromatography is often employed for the separation of thermally unstable compounds which cannot easily be ionized in a conventional ion source without decomposition or fragmentation. Although many techniques for the ionization of compounds of this type are now available, e.g., field desorption and neutral particle or ion bombardment secondary ion mass spectrometry, most of these methods require the sample to be coated on an emitter or target, and are consequently unsuited for the ionization of the eluent from a liquid chromatograph. It is highly desirable, therefore, that any method of interfacing a liquid chromatograph to a mass spectrometer should incorporate a method of ionizing samples which are thermally unstable or involatile. Several interfacing methods which fulfil these requirements are known, and the present invention is concerned with the method known as thermospray ionization, which has been developed chiefly by M. L. Vestal and his coworkers.

The first practical version of this interface an ion source is described in International patent application publication No. 81/03394. In the method, the eluent from the liquid chromatograph is passed through a capillary tube which is heated, typically to red heat, by means of four oxy-hydrogen torches, so that a jet of solvent vapour containing particles of sample is formed in a region of reduced pressure downstream of the end of the capillary tube. A conical skimmer containing a small hole in the centre is used to intercept the jet thus formed, and the vapour emerging through the hole (which contains a greater proportion of sample molecules) enters a tubular channel, also maintained at a reduced pressure, where it impinges on a heated target situated downstream of the skimmer. An ion vapour is supposedly formed at this point and ions characteristic of the dissolved sample leave the tubular chamber through a hole in its wall adjacent to the heated target and are mass analyzed by a mass filter situated in a region of high vacuum. Surprisingly, the resultant mass spectra show no evidence of thermal decomposition, even when thermally unstable samples are analyzed, and this is ascribed to the very short time of passage through the interface and to the protection of the sensitive molecules from exposure to the very high temperatures by virtue of the evaporating solvent molecules. In the patent application, emphasis is placed on the presence of the heated target, and the inventors claim that ionization of sample molecules takes place by an imperfectly understood process associated with the collision of the molecular beam of solvent molecules and solvated sample molecules with the heated surface of the target. Later work by C. R. Blakley and M. L. Vestal, described in Analytical Chemistry, 1983, vol. 55, p 750, showed that in fact the heated target could be omitted, and that ions were formed in the spray emerging from the heated capillary. The apparatus was also simplified by omission of the conical skimmer and the region of reduced pressure between it and the capillary nozzle. In this simplified version, the solution to be analysed is pumped through a strongly heated capillary tube which protrudes into a wider bore tube maintained at a pressure of between 1 and 10 torr by means of a mechanical vacuum pump. A spray of evaporating solvent droplets containing ions and molecules of the solvent is formed in the wider bore tube. A small hollow cone with a hole in its apex is positioned through the wall of the tube downstream of the end of the capillary with its axis at right angles to that of the spray and with its apex just short of the centre of the tube. The hole in the apex of the cone leads to the high vacuum part of the mass spectrometer, and ions passing through it enter the mass filter. The walls of the tube enclosing the spray and the sampling cone are advantageously heated.

The thermospray method described is quite distinct from the earlier method of connecting a liquid chromatograph and a mass spectrometer in which the eluent was directly introduced into the source of a conventional chemical ionization mass spectrometer, through a heated capillary, for example as described in U.S. Pat. No. 3,997,298. In ion sources of this kind, ionization of the sample is effected by reaction of the sample molecules with a plasma of ions formed from the solvent vapour by means of collisions with a beam of electrons inside the source. It is also distinct from liquid analyzing mass spectrometers based on techniques such as electrospray or electrohydrodynamic ionization, for example as described in U.S. Pat. Nos. 4,160,161, 4,209,696, and 4,144,451, in which ionization is effected by means of a high electrical potential applied between the capillary tube and a counter electrode situated opposite its end. In these systems a spray of charged droplets is generated as the liquid emerges from the capillary tube under the influence of the electrical field, and these droplets gradually evaporate leaving ions, usually clustered with solvent molecules, which are caused to pass through a hole in the counter electrode into a mass filter.

A possible explanation of the mechanism of thermospray ionization has been offered by M. L. Vestal in the International Journal of Mass Spectrometry and Ion Physics, 1983, vol. 46, pps. 193-6, where it is suggested that ions already present in the solution evaporate in solvated form from droplets in the thermally produced spray. For example, if the solution to be analyzed consists of the sample dissolved in a solution of ammonium acetate, primary ions of $NH_4^+$ and $CH_3COO^-$ are formed in the spray. These ions can react with sample molecules forming $NH_4^+$ or $CH_3COO^-$ adducts, which can be analysed by the mass spectrometer. In some cases, $(M+H)^+$ ions or $(M-H)^-$ ions are formed, especially when the sample molecule M is relatively low molecular weight and neutral in solution, presumably by a mechanism similar to that of conventional chemical ionization. This mechanism implies that optimum conditions for thermospray ionization occur when the liquid chromatograph eluent contains ions such as $NH_4^+$ and $CH_3COO^-$, and this is found to be the case. Fortunately, mobile phases containing salts are commonly employed in the liquid chromatography of biochemicals, and consequently the method is very useful in this field. It is found that the best results for high molecular weight thermally unstable compounds are obtained when the compounds are ionized in the solution of the eluent, and rather poorer results are obtained with high molecular weight samples which are electrically neutral in solution. Indeed, many molecules of this type cannot be successfully ionized by the method. Even when the method produces good results, the ions formed from high molecular weight compounds are usually clustered with a variety of species derived from the mobile phase, which increases the difficulty of spectrum interpretation. Further, all prior art forms of the thermospray method rely on the diffusion of sample ions through the small hole in the sampling cone, along an axis at right angles to the direction of the spray. This method of sampling reduces the number of neutral molecules entering the high vacuum part of the mass spectrometer, which leads to a simplification of the pumping system, but it is relatively inefficient because the majority of the ions formed will be carried past the sampling cone by the motion of the molecules in the spray.

It is an object of the present invention to provide a mass spectrometer having a thermospray type liquid ionization source which incorporates means for improving the efficiency of sampling the ions in the spray, and additionally to improve the efficiency of ionization, especially of samples of high molecular weight which are electrically neutral in solution, thereby increasing the sensitivity of the apparatus. It is a further object of the invention to provide a mass spectrometer having a thermospray type liquid ionization source in which the proportion of ions formed by the addition to or abstraction from the sample molecule of a proton is increased relative to that of the cluster ions which are predominantly formed with prior art thermospray type ion sources, and to increase in a controlled way the proportion of fragment ions formed by decomposition of the primary ions produced in the spray, so that interpretation of the resulting spectra may be facilitated and the determination of the molecular weight and the structure of the sample may be made more certain.

SUMMARY AND DETAILED DESCRIPTION OF THE INVENTION

Thus according to one aspect of the invention, there is provided mass spectrometer having an ion source comprising a spraying chamber, spraying means for thermospraying a liquid sample into said chamber, a sampling aperture arranged in a wall of said chamber and provided with conduit means connectible with the entrance aperture of a mass analyser, whereby ions passing through said sampling aperture may be led into said mass spectrometer, electrode means capable of generating in said chamber an electrostatic field capable of retarding and deflecting into said sampling aperture ions in the thermospray formed by said spraying means, and means for maintaining said chamber at sub-autmospheric pressure; said sampling and conduit means being so arranged that their axis at said sampling aperture is at an angle of at least 30° to the axis (hereinafter the "spay axis") of said spraying means at the outlet thereof into said chamber and said sampling aperture being arranged in displaced facing arrangement with said spray axis.

In one preferred embodiment, the electrode means is arranged downstream of the sampling aperture, i.e. the sampling aperture is located intermediately of the electrode means and the outlet of the spraying means.

Viewed from one aspect, the invention thus provides a mass spectrometer for the analysis of a liquid sample having an ion source comprising:

(a) a spraying chamber;

(b) a first conduit means for conveying a said liquid sample from a pumping means to an atomizing nozzle having an axis and an orifice, said nozzle being disposed in an end wall of said spraying chamber and being directed into said spraying chamber;

(c) a vacuum pump connected by a second conduit means to said spraying chamber, said vacuum pump being capable of maintaining the pressure in said spraying chamber substantially less than atmospheric pressure;

(d) a heater which is capable of raising the temperature of said atomizing nozzle to at least the value required for a spray containing ions characteristic of said liquid sample to be formed;

(e) a sampling aperture disposed in a side wall of said spraying chamber, downstream of said atomizing nozzle, leading to a mass analyzer having an entrance aperture situated in a region in which the pressure is maintained at less than about $10^{-3}$ torr, said sampling aperture and said entrance aperture defining an axis which is arranged to be inclined at at least 30° to said axis of said atomizing nozzle;

(f) at least one electrode capable of generating a repulsive electrostatic field in said spraying chamber, said field being capable of retarding and deflecting into said sampling aperture ions characteristic of said liquid sample, and said electrode being at least one electrode capable of generating a repulsive electrostatic field, said field being capable of retarding and deflecting into said sampling aperture from said chamber ions characteristic of said liquid sample, and said electrode being so disposed that the highest electrical potential in said field is situated substantially downstream of said sampling aperture disposed that the highest electrical potential in said field is situated substantially opposite to said sampling aperture.

In an alternative aspect, the electrode or electrodes (f) are so disposed that the highest electrical potential in said field is situated substantially downstream of said sampling aperture.

Preferably the nozzle heater should be capable of raising the temperature of the nozzle to at least 500° C., and an additional heater advantageously is provided to heat the walls of the chamber in which the spray is formed to about 400° C. Advantageously both heaters are powered by variable power supplies so that the temperatures may be adjusted to obtain the optimum conditions for thermospray evaporation and ionization to take place, as described by M. L. Vestal in the references given above. Several thermocouples attached to the nozzle heater, spray chamber and other parts of the apparatus are also desirable to assist the setting up process.

The sampling aperture may advantageously be formed as a small hole in the apex of a hollow cone which is inserted through a larger aperture in the wall of the spraying chamber so that the apex of the cone is just short of the centre line of the nozzle, as described by Vestal. Preferably the axis defined by the apex of the cone and the extrance aperture of the mass filter should lie at right angles to the axis of the nozzle. Also following the teachings of Vestal, the spray chamber is preferably pumped through a large bore pipe connected to a port on the wall of the chamber situated directly opposite to the nozzle, so that most of the solvent molecules enter the pipe and are efficiently removed from the chamber.

The mass spectrometer of the invention is preferably provided with means for applying to the retarding electrode(s) a potential which is selected to optimize transmission through the sampling aperture of ions present in the spraying chamber; this suitably comprises an electrical potential generating means capable of maintaining the electrode at a potential of the same polarity as that of the ions to be analyzed and at a value selected to ensure optimum transmission of at least some of the ions formed in said spray through said sampling aperture into said mass analyzer.

The mass analyzer employed in the mass spectrometer may be of any suitable type, but a quadrupole analyzer is most convenient. The ions produced by the source are of low energy and can conveniently be analyzed by a quadrupole filter. A magnetic sector filter may be used, but would require the ions to be generated at a higher potential, or for the energy of the ions to be increased after they have been generated. Several ways of achieving this are possible.

By the provision of a suitable repulsive electrostatic field in the spraying chamber of the ion source, ions formed in the spray are retarded and deflected through the sampling aperture into the mass filter. This process is more efficient than the diffusion relied on in the prior art thermospray ion sources, and does not increase the pressure in the mass filter region of the mass spectrometer because the neutral solvent molecules are not deflected by the field.

The electrode means used to generate the electrostatic repulsive field may take any convenient form. Usually the highest repulsive potential will be situated on the opposite side of the spray axis from the sampling aperture. A convenient form consists of a single rod-like electrode fitted through a bush in the wall of the spray chamber, opposite to the sampling aperture but displaced downstream from it by a suitable distance, typically 3-4 mm, assuming the nozzle and chamber to be dimensioned according to Vestal. The electrode rod preferably protrudes into such a chamber by approximately 2-5 mm. The exact position, size and shape of the electrode are not particularly critical, but the field should preferably be adjusted so that the trajectories of the ions entering it in the direction of the spray are deflected through the sampling aperture. The potential applied to the electrode must of course be the same polarity as that of the ions to be monitored, so that those ions are repelled by the field. As the thermospray can generate both positive and negative ions, it is advantageous to use an electrode power supply that can generate either positive or negative voltages. The potential on the electrode has been found to vary the nature of the spectrum, as explained below, as well as affecting the transmission efficiency of ions into the mass filter. To some extent, the effect of changing the position of the electrode can be compensated by varying the potential applied to it, but it will be appreciated that an electrode system designed to produce a field which will effectively focus the ions through the sampling aperture will be the most effective. However, the improvement produced by use of a special electrode system will in many cases be small, and may not be worth the additional complication.

As stated above, the nature of the spectrum produced by thermospray ionization using the invention is changed, usually advantageously. Thus in a yet further aspect the invention provides a method of analyzing a liquid sample comprising thermospraying said sample into a spraying chamber having a sampling aperture, maintaining said spraying chamber at a subatmospheric pressure, and mass analyzing ions formed from said sample which have passed through said sampling aperture, the improvement comprising generating in said spraying chamber a repulsive electrostatic field capable of retarding and deflecting said ions through said sampling aperture.

Viewed from another aspect, the invention provides a method of analyzing a liquid sample in a mass spectrometer equipped with a thermospray ion source, in which method said sample is pumped through a strongly heated atomizing nozzle and is vaporized and at least partly ionized as it emerges in the form of a spray into a first region maintained at a subatmospheric pressure, and in which at least some of the ions present in said first region pass through a sampling aperture into a mass analyzer contained in a second region maintained at a pressure of less than $10^{-3}$ torr, the improvement comprising generating a repulsive electrostatic field in said first region and adjusting the magnitude of said field in order to optimize the generation and transmission into said mass analyzer of ions selected from the group comprising:

(a) ions formed by the addition of a proton to, or abstraction of a proton from, molecules contained in said liquid sample;

(b) ions formed by the fragmentation of molecules contained in said liquid sample; and (c) cluster or adduct ions formed from molecules contained in said liquid sample by association of ions formed from said molecules with other molecules present in said first region.

In a preferred embodiment, the method of the invention comprises:

(a) causing a sample solution to flow through a nozzle having a small orifice;

(b) strongly heating said nozzle so that vaporization and ionization of at least some of said solution takes place as it emerges in the form of a spray from said nozzle into a first region;

(c) maintaining said first region at a subatmospheric pressure by means of a vacuum pump;

(d) maintaining a second region adjacent to said first region at a pressure of less than $10^{-3}$ torr;

(e) causing at least some of the ions formed in said spray to pass through an aperture in a wall between said first and second regions into a mass analyzer situated in said second region, along an axis inclined at 30° or more to the axis of said spray, by means of a suitable electrostatic field generated in said first region and arranged so that said field repels said ions and so that the highest electrical potential in said field exists at a point downstream of said aperture;

(f) selecting the shape and magnitude of said electrostatic field to optimize either the generation and transmission to said mass analyzer of ions corresponding to the addition of a proton to, or abstraction of a proton from, a molecule of a sample contained in said solution, or the generation and transmission to said mass analyzer of ions formed by decomposition of the cluster ions initially formed in said spray.

As explained, the ions formed in the spray are retarded by the field and consequently spend more time in the region of the spray before entering the sampling aperture. This changes the nature of the ion-molecule reactions which take place before the ions are mass analyzed, and it is found that in general the formation of cluster ions is inhibited and the formation of pseudomolecular ions by the addition or abstraction of a proton is enhanced. Additionally, because the change in the mechanism of ionization brought about by use of the invention, the range of molecules which can be successfully analyzed by the thermospray method is extended to include many large molecules which are electrically neutral in solution, and which cannot be analysed with prior art thermospray systems.

The field required is most conveniently produced by use of the electrode system described previously. A single electrode downstream of the sampling aperture is usually adequate, and the potential on this electrode determines the extent of the change in the ionization mechanism. In general, the higher the potential the greater the proportion of $(M+H)^+$ or $(M-H)^-$ ions in the spectrum (where M represents a sample molecule), relative to the cluster ions of M with $(NH_4)^+$ or $(CH_3COO)^-$ ions, which are characteristic of the spectra normally obtained with prior art thermospray sources when a solvent containing ammonium acetate is used. In addition, as previously explained, the sensitivity is invariably higher when the pseudomolecular ions rather than the cluster ions are monitored.

The potential necessary to achieve this change in ionization mechanism, and the extent of the change so caused, is dependent mainly on the chemical nature of the sample and the mobile phase, and to a lesser extent on the position and shape of the electrode. It is found that when samples which give intense cluster ions when ionized by prior art thermospray sources are run on a spectrometer constructed according to the invention, the nature of the spectrum can be changed from domination by cluster ions to domination by pseudomolecular ions simply by increasing the electrode potential. The pseudomolecular ions are usually of greater intensity than the cluster ions, so that the sensitivity of the method is enhanced and the determination of the molecular weight of the sample is facilitated. In many cases, fragment ions of lower molecular weight than the sample are also formed, but the pseudomolecular ion is almost always present, unlike conventional electron impact spectra. The presence of these fragment ions can assist the determination of the structure of the sample molecule. In the case of high molecular weight samples which are electrically neutral in solution, which cannot be successfully ionized by prior art thermospray spectrometers, use of the invention often results in the formation of intense pseudomolecular ions, so that the invention can also be used to extend the range of compounds which can be analyzed by thermospray mass spectrometry. However, if the potential on the electrode is increased too much, then the focussing action of the field is reduced, and the intensity of all the ions in the spectrum begins to decrease. There exists an optimum setting, therefore, for maximum sensitivity to be obtained, and this usually corresponds with an enhanced formation of pseudomolecular ions and fragment ions at the expense of cluster ions. It is dependent on the chemical nature of the sample and the mobile phase. The extent of fragmentation, when it occurs, is also increased by increasing the electrode potential.

Although the main purpose of the invention is to increase the proportion of pseudomolecular ions in the spectrum of a sample and to increase the sensitivity, there nevertheless exists the possibility of operating the electrode at a potential less than optimum so that cluster ions still dominate the spectrum, if it is desired to record these. With many samples, operation in this way is still preferable to operation without the electrode because the focussing action of the field results in a considerable increase in sensitivity.

The inventors do not claim to fully understand the mechanism by which the invention operates. However, the electrical field downstream of the sampling aperture is thought to retard the cluster ions initially formed in the spray and consequently increase the time they spend in a region where the pressure is relatively high, and the concentration of solvent ions is also high. The number of molecular collisions of sufficient energy to desolvate the cluster ions is therefore greatly increased, and there is more time for neutral sample molecules to be ionized by collision with retarded solvent ions, which would lead to pseudomolecular ions of the sample, as in a conventional chemical ionization source. Fragment ions will also be formed if the energy of some of the collisions is sufficient to break bonds in the sample molecules as well as the cluster ion-sample molecule bonds If the field is correctly shaped, then it will also exert a focussing action and deflect ions through the sampling aperture into the mass filter. It will be noted that a convex field formed downstream of the aperture can act in a similar way to a convex mirror, and can focus ions of the correct energy through the sampling aperture on to the entrance aperture of the mass filter. This energy filtering action is thought to contribute to the domination of the spectrum by one type of ion at the expense of the other, depending on the potential chosen. It is also clear that for optimum focussing action, the field generating electrode or electrodes must be situated downstream of the aperture so that the field can act as a mirror. Fields centered on the axis of the sampling aperture, or parallel to the spray axis, are thought to be less satisfactory.

BRIEF DESCRIPTION OF THE DRAWINGS

A preferred embodiment of the invention will now be described by way of example with reference to the accompanying drawings, in which.

DETAILED DESCRIPTION OF THE INVENTION

Figure 1:
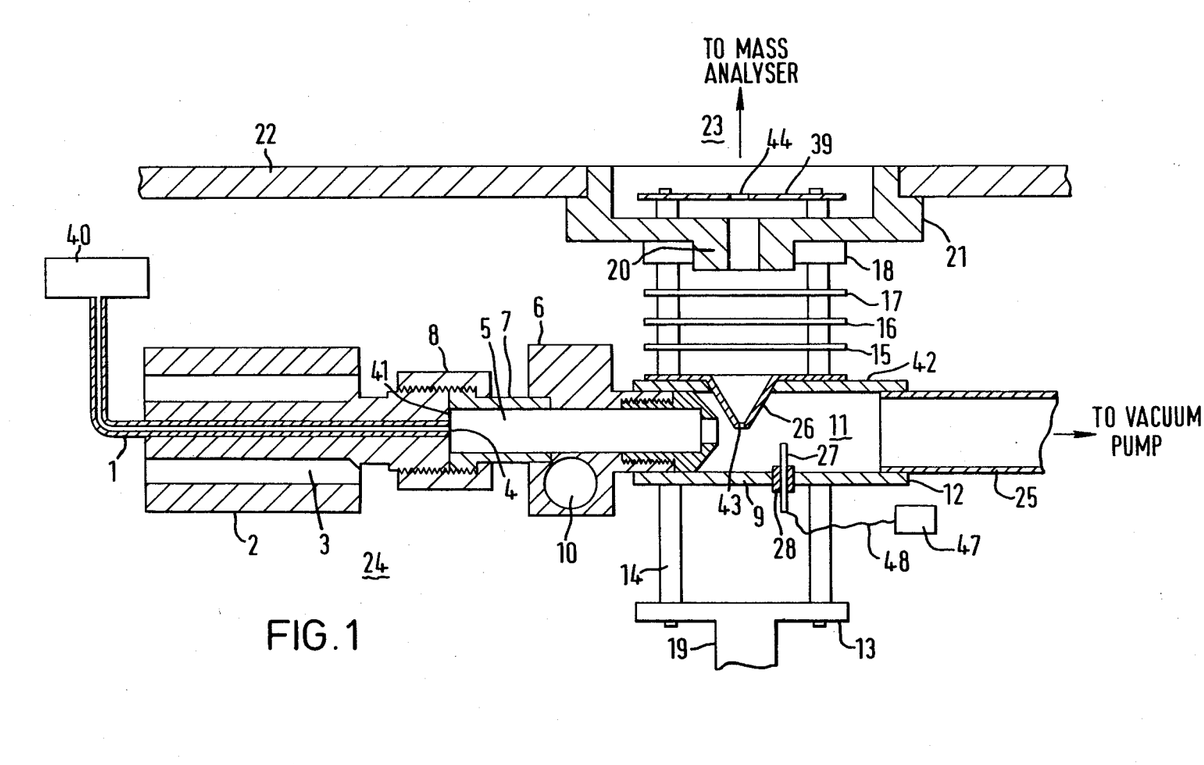
FIG. 1 is a schematic drawing of part of a mass spectrometer constructed according to the invention and having a rod-like electrode downstream of the sampling aperture.

Referring first to FIG. 1, the eluent from a liquid chromatograph is pumped by pumping means 40 through capillary tube 1, typically 0.15 mm bore, which is brazed securely in a close fitting hole in copper block 2. This contains four holes 3 into which electrical cartridge heaters, typically 100 W, are inserted. These heaters are capable of raising the temperature of capillary tube 1 to at least 500° C. The capillary tube 1 terminates at an atomizing nozzle 4 in the end wall 41 of chamber 5 (about 10 mm diameter) which is formed inside another heated copper block 6, adaptor 7 and jet 9, the aperture of which is about 3.5 mm diameter. Adaptor 7 is secured to block 2 by nut 8 and is brazed into block 6 as shown. Another 100 W cartridge heater is inserted in hole 10 in block 6.

The cylindrical ion chamber 11 is an extension of chamber 5 and is formed in a stainless steel block 12. This is supported from plate 13 by four insulating rods 14, which also carry the focussing electrodes 15, 16, 17 and locating ring 18, spaced apart by insulating spacers. Rods 14 and the insulating spacers are preferably made from ceramic. Plate 13 is in turn supported by tube 19 from the mounting flange of the ion source assembly (not shown) which is in turn attached to the end flange of the source housing of the spectrometer. Jet 9 is an easy fit in ion chamber 11 so that the assembly of blocks 2 and 6 can easily be separated from the ion source assembly.

Locating ring 18 engages with spigot 20 on flange 21 which is in turn fitted to diaphragm 22, which divides the interior of the source housing into two regions, a high vacuum region 23 in which the mass analyzer, e.g. a mass filter, is situated, and a lower vacuum region 24 containing the ion source. Ion chamber 11 is pumped by a large bore pipe 25 which passes through the wall of the source housing and incorporates both a flexible section and a separable connector. A large mechanical rotary vacuum pump, typically 5 l.s$^{-1}$, is used to evacuate chamber 11 through pipe 25.

A hollow stainless steel cone 26 has a small hole, approximately 0.5 mm diameter, in its apex, which serves as sampling aperture 43. Cone 26 is positioned through a hole in the side wall 42 of the block 12 so that it protrudes into chamber 11. A quadrupole mass filter (not shown) is positioned in region 23 and its entrance aperture 44, formed in plate 39, is insulated from the earthed vacuum system. This allows the entrance aperture and the quadrupole filter to be maintained at the ion accelerating voltage required by the filter, thereby permitting ion chamber block 12 to be earthed. Typically the filter and plate 39 will be maintained at $-5$ V when positive ions are analyzed. Focussing electrodes 15, 16, 17, each with a suitable aperture at the centre, are provided between sampling cone 26 and the entrance aperture of the filter. These are maintained at adjustable potentials of polarity opposite to that of the ions to be analysed, which are selected to optimize the sensitivity.

Figure 5:
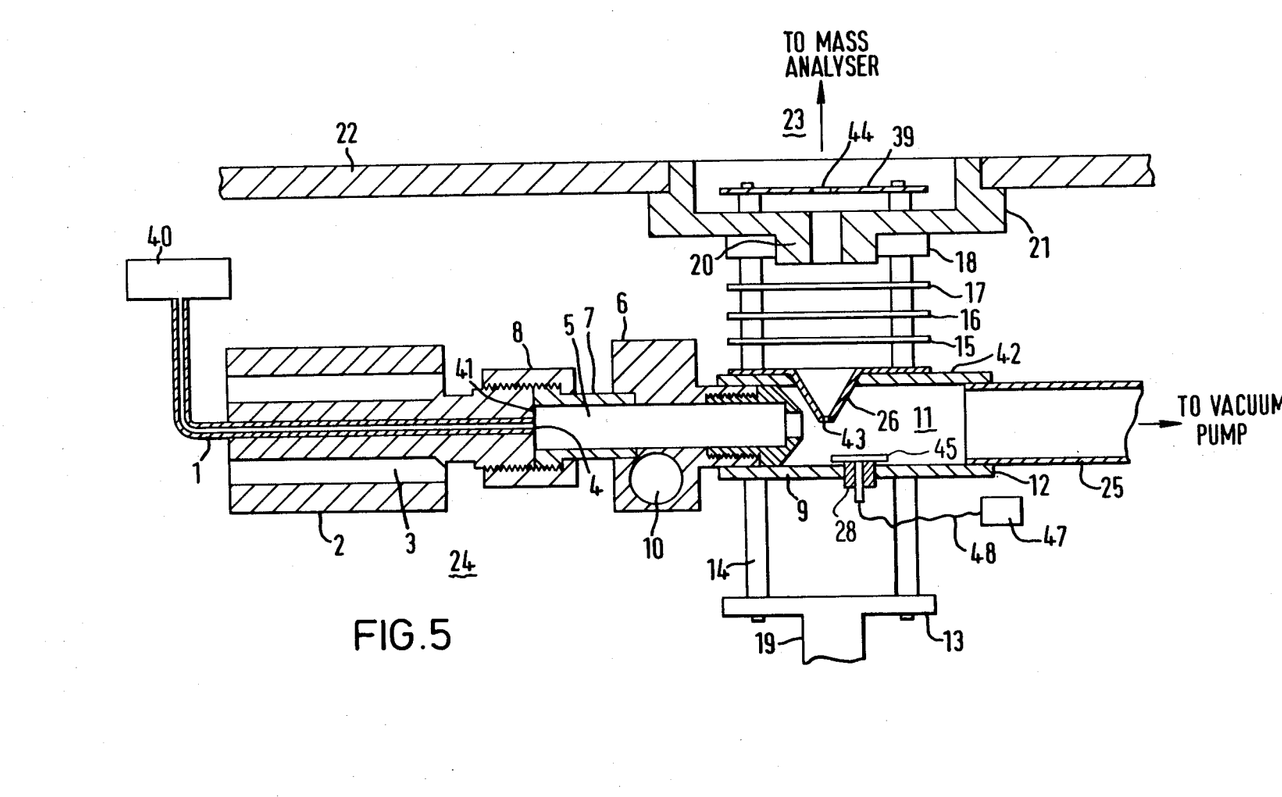
FIG. 5 is a schematic drawing of part of a mass spectrometer constructed according to the invention and having a plate-like electrode.

In a preferred embodiment, a rod-like electrode 27 is fitted through an insulated bush 28 in the wall of ion chamber block 12, as shown in FIG. 1. The electrode may consist of a short copper or stainless steel rod about 0.5 mm in diameter situated 3 mm downstream of the aperture in sampling cone 26 which protrudes into chamber 11 to a position just short of the centre line of jet 9. A potential is applied to electrode 27 by potential applying means 47 which is shown schematically linked to electrode 27 by lead 48. Electrode 27 is maintained at an adjustable potential of the same polarity as the ions to be analyzed. Typically this may lie between 50 and 500 volts in the case of positive ions, dependent on the type of spectrum required. An alternative form of the electrode is shown in FIG. 5, which shows a plate-like electrode 45 disposed with a major surface substantially parallel to the axis of the atomizing nozzle 4. Electrode 45 is insulated from block 12 by bushing 28 and attached to potential applying means 47 by lead 48.

Figure 2:
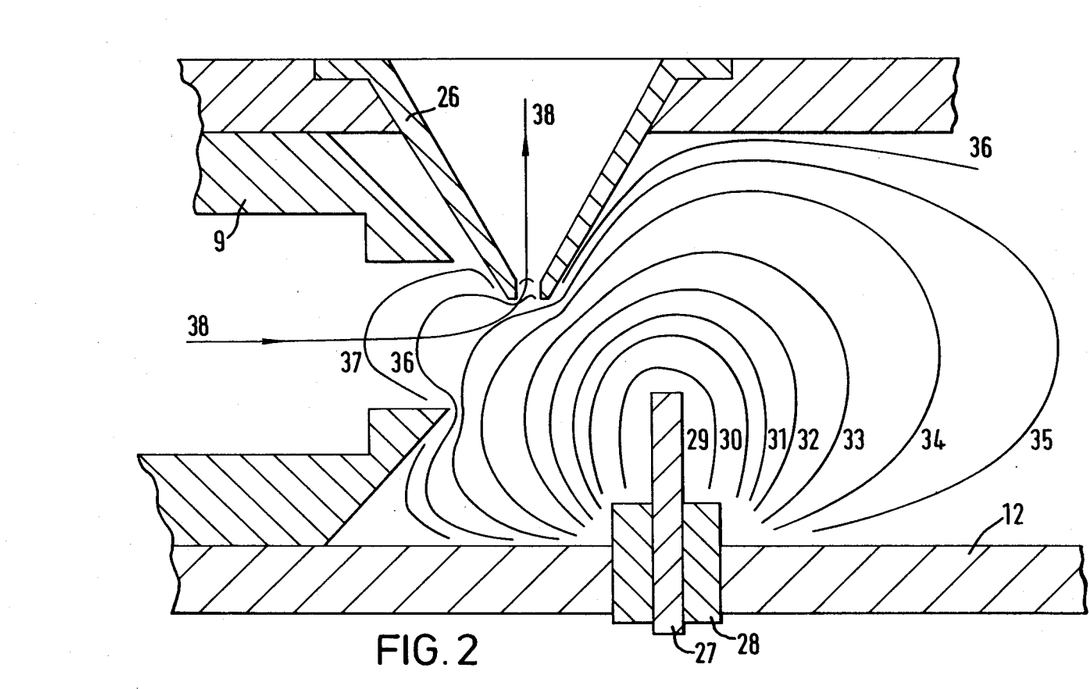
FIG. 2 shows the lines of equipotential generated by an electrode situated downstream of the sampling aperture as shown in FIG. 1.

FIG. 2 illustrates the form of the electrostatic field generated by the electrode 27. Curves 29–37 are lines of equipotential representing 50%, 40%, 30%, 20%, 10%, 5%, 2%, 1%, and 0.5% respectively of the potential existing between electrode 27 and the walls of chamber 11. Curve 38 represents a probable trajectory of an ion of the same polarity as the potential applied to electrode 27 which enters the field with a translational energy along the axis of the thermospray jet. As it approaches the electrode 27 it is retarded by the field and its direction of motion is turned away from the most intense part of the field until its translational energy in the axial direction is converted to potential energy. The ion will then follow the second part of trajectory 38, where it is accelerated by the field through the hole in cone 28 and subsequently into the mass filter. The translational energy of the ions formed in the thermospray is largely determined by molecular collisions in the spray as it is formed, so that the spread in translational energies of the ions as they approach the field due to electrode 27 will be relatively small. A large proportion of the ions will therefore be turned at approximately the same point in the field, and will pass through the hole in cone 26, and consequently the efficiency of transfer of the ions into the filter is increased. Further, as the ions are retarded they will undergo more collisions with neutral molecules in the spray which are unaffected by the field, and this will lead to an increased contribution from declustering and fragmentation reactions, as well as an increased tendency for the formation of pseudomolecular ions, as explained previously.

The process of focussing the ions through the hole in cone 26 is assisted by virtue of the flow of gas from the relatively high pressure region 11 into the lower pressure region 24 which extends into cone 26. This flow of molecules will impart translational energy in the required direction to the ions by collisions with the neutral molecules entering the hole by virtue of the pressure difference across it. This process is the only process operating in a prior art thermospray ion source, apart from the small degree of penetration of the electrical field due to electrode 15 through the hole in cone 26, and is relatively inefficient. This is illustrated by the relatively poor sensitivity exhibited by prior art thermospray mass spectrometers in comparison with the spectrometer of the present invention.

Although the simplest embodiment of the invention involves a single electrode downstream of the sampling orifice, it will be appreciated that a different configuration of electrodes can be used, providing that they generate a repulsive field centered downstream of the sampling orifice which deflects the ions in the required manner. For example, a field generated by means of flat (or preferably convex) plate-like electrode situated downstream of the orifice and inclined to the wall 12 so that it is approximately parallel to the wall of cone 26 could also be used. Such an electrode would generate a field similar to the one shown in FIG. 2 in the vicinity of jet 9 and aperture 26, but may reducethe pumping speed by obstructing pipe 25. A mesh electrode could be used to minimize this problem. Other suitable electrode configurations will occur to those skilled in the art.

Figure 3A:
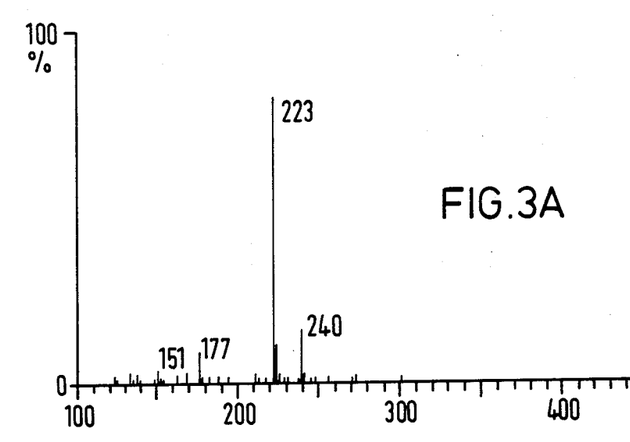
FIG. 3A shows the spectrum of diethyl phthalate dissolved in a mobile phase consisting of 40% 0.1 M ammonium acetate and 60% methanol run on the apparatus of FIG. 1 with a very low electrode potential.
Figure 3B:
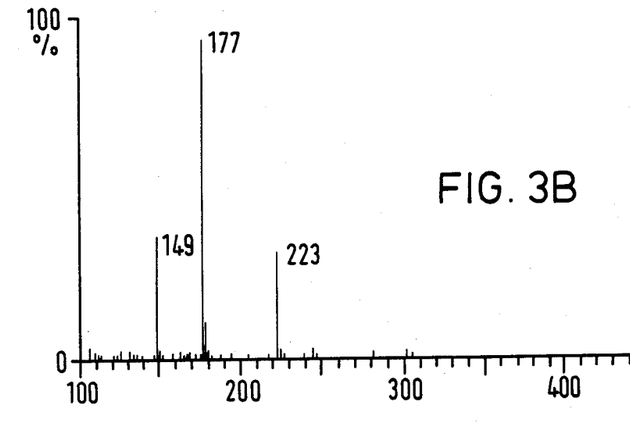
FIG. 3B shows the same compound run under the same conditions with a higher electrode potential.

FIGS. 3A and 3B, and 4A and 4B, illustrate the change in the nature of the observed spectra that can be brought about by use of the invention. FIG. 3A is the spectrum of diethyl phthalate (M.Wt. 222) obtained using a mobile phase of 40% 0.1 M ammonium acetate, 60% methanol, and using the apparatus of FIG. 1 with a very low potential applied to electrode 27, insufficient to bring about any change in the type of spectrum from that obtained using a conventional thermospray spectrometer. It can be seen that the major ion in the spectrum is the $(M+H)^+$ ion at m/e=223, with a less intense cluster ion at m/e=240 which represents $(M+NH_4)^+$. There is no trace of an ion at m/e=149, which is an ion highly characteristic of the electron impact spectrum of any phthalate. In contrast, the spectrum of the same compound run on the same instrument using a higher electrode potential, FIG. 3B, shows the $(M+H)^+$ ion at m/e=223 and an intense phthalate ion at m/e=149, as well as a fragment ion at m/e=177 (loss of $C_2H_5OH$). There is no trace of the cluster ion at m/e=240. The spectrum of FIG. 3B is more easily interpreted than that of FIG. 3A and its use would lead to a more reliable identification of the sample.

Figure 4A:
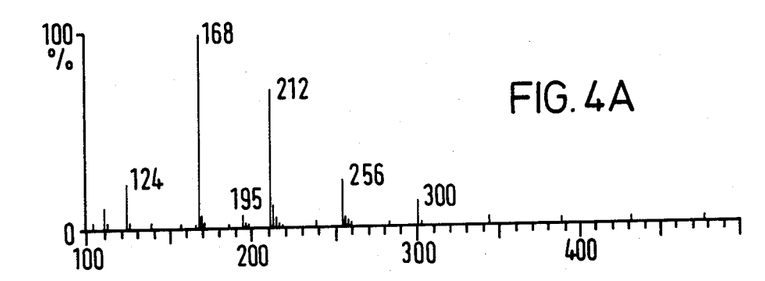
FIG. 4A shows the spectrum of a polyethylene glycol (Carbowax 200) run under the conditions of FIG. 3A.
Figure 4B:
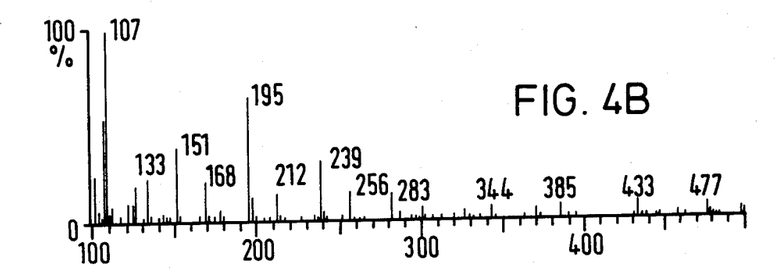
FIG. 4B shows the sample of FIG. 4A run under the conditions of FIG. 3B.

FIG. 4A shows the spectrum of a polyethylene glycol mixture containing polymeric molecules of different chain lengths run on an apparatus constructed according to the invention but operated with a low potential (+90 V) on the electrode 27. The peaks at m/e=124, 168, 212, 256, and 300 represent cluster ions of the form $[(HO-(CH_2CH_2O)_n-H)+NH_4]^+$, where n=2, 3, 4, 5, or 6, respectively. In contrast, FIG. 4B shows the spectrum of the same mixture run with a higher electrode potential (250 v) on electrode 27. The ions at m/e=107, 151, 195, 239, and 283 represent pseudomolecular ions of the form $[(HO-(CH_2CH_2O)_n-H)+H]^+$, with n=2, 3, 4, 5, or 6, respectively. These results illustrate the change in nature of the spectrum from domination by cluster ions to domination by pseudomolecular ions as the potential on the electrode is increased. In the case of FIG. 4A, the spectrum is identical to that which would be obtained with a conventional thermospray mass spectrometer, such as described by Blakley and Vestal, and the relatively low electrode potential (90 v) serves only to improve the efficiency of the transmission of the ions into the mass filter without changing the nature of the spectrum.

We claim:

1. A mass spectrometer for the analysis of a liquid sample having an ion source comprising:
   (a) a spraying chamber;
   (b) a first conduit means for conveying the liquid sample from a pumping means to an atomizing nozzle having an axis and an orifice, said nozzle being disposed in an end wall of said spraying chamber and being directed into said chamber;
   (c) a vacuum pump connected by a second conduit means to said spraying chamber, said vacuum pump being capable of maintaining the pressure in said spraying chamber substantially less than atmospheric pressure;
   (d) a heater which is capable of raising the temperature of said atomizing nozzle to at least the value required for a spray containing ions characteristic of said liquid sample to be formed;
   (e) a sampling aperture disposed in a side wall of said spraying chamber, downstream of said atomizing nozzle, leading to a mass analyzer having an entrance aperture situated in a region in which the pressure is maintained at less than about $10^{-3}$ torr, said sampling aperture and said entrance aperture defining an axis which is arranged to be inclined at at least 30 to said axis of said atomizing nozzle;
   (f) at least one electrode capable of generating a repulsive electrostatic field, said field being capable of retarding and deflecting into said sampling aperture from said chamber ions characteristic of said liquid sample, and said electrode being disposed in said spraying chamber downstream of said sampling aperture for generating the highest electrical potential of said field downstream of said sampling aperture.

2. A mass spectrometer according to claim 1 in which said heater is capable of raising the temperature of said atomizing nozzle to at least 500° C., said vacuum pump is capable of maintaining the pressure in said spraying chamber at $10^{-3}$ torr or less, and said sampling aperture is formed as a small hole in the apex of a hollow cone inserted through said side wall.

3. A mass spectrometer according to claim 1 in which said electrode comprises a rod-like electrode disposed with its longest axis substantially perpendicular to said axis of said atomizing nozzle.

4. A mass spectrometer according to claim 1 in which said electrode comprises a plate-like electrode with a major surface substantially parallel to said axis of said atomizing nozzle.

5. A mass spectrometer according to claim 1 comprising means for applying to said electrode a potential selected to optimize transmission through said sampling aperture of ions present in said spraying chamber.

6. In a method of analyzing a liquid sample comprising thermospraying said sample from a heated atomizing nozzle into a spraying chamber having a sampling aperture downstream of said atomizing nozzle, maintaining said spraying chamber at a substmospheric pressure, and mass analyzing ions formed from said sample which have passed through said sampling aperture, the improvement comprising generating in said spraying chamber by the action of an electrode disposed downstream of said sampling aperture a repulsive electrostatic field having its highest electrical potential downstream of said sampling aperture and being capable of retarding and deflecting said ions through said sampling aperture.

7. In a method of analyzing a liqiud sample in a mass spectrometer equipped with a thermospray ion source, in which method said sample is pumped through a strongly heated atomizing nozzle and is vaporized and at least partly ionized as it emerges in the form of a spray into a first region maintained at a subatmospheric pressure, and in which at least some of the ions present in said first region pass through a sampling aperture disposed downstream of said atomizing nozzle into a mass analyzer contained in a second region maintained at a pressure of less than $10^{-3}$ torr, the improvement comprising generating in said first region by the action of an electrode disposed downstream of said sampling aperture a repulsive electrostatic field downstream of said sampling aperture and adjusting the magnitude of said field in order to optimize the generation and transmission into said mass analyzer of ions selected from the group comprising:
  (a) ions formed by the addition of a proton to, or abstraction of a proton from, molecules contained in said liquid sample;
  (b) ions formed by the fragmentation of molecules contained in said liquid sample; and
  (c) cluster or adduct ions formed from molecule contained in said liquid sample by association of ions formed from said molecules with other molecules present in said first region.

* * * * *